(12) United States Patent
Ueno et al.

(10) Patent No.: US 6,476,039 B1
(45) Date of Patent: Nov. 5, 2002

(54) OPHTHALMIC COMPOSITION

(75) Inventors: Ryuji Ueno, Montgomery, MD (US); Ichie Kato, Kawanishi (JP)

(73) Assignee: R-Tech Ueno, Ltd., Osaka-fu (JP)

( * ) Notice: Subject to any disclaimer, the term of this patent is extended or adjusted under 35 U.S.C. 154(b) by 0 days.

(21) Appl. No.: 10/133,450

(22) Filed: Apr. 29, 2002

Related U.S. Application Data

(63) Continuation of application No. 09/485,414, filed as application No. PCT/JP99/00369 on Jan. 29, 1999, now Pat. No. 6,403,598.

(30) Foreign Application Priority Data

Jan. 30, 1998 (JP) .............................................. 10-19836

(51) Int. Cl.[7] .............................................. A61K 31/505
(52) U.S. Cl. ........................ 514/258; 514/259; 514/912
(58) Field of Search ................................ 514/258, 259, 514/912

(56) References Cited

FOREIGN PATENT DOCUMENTS

| EP | 0 124 327 A | 11/1984 |
|----|-------------|---------|
| EP | 0 170 237 A | 2/1986 |
| EP | 0 218 999 A | 4/1987 |
| EP | 0 719 767 A | 7/1996 |
| JP | 01 125322   | 8/1989  |

OTHER PUBLICATIONS

Shizuo Ao Et Al.: "Effect of a Novel Aldose Reductase Inhibitor "FR74366" on Diabetic Cataract" Int. Congr. Ser.—Excerpta Medica, 1990, pp. 221–224, XP002110639 the whole document (Copy submitted to USPTO by WIPO).

Mamoru Matsuda Et Al.: "The effects of aldose reductase inhibitor on the corneal endothelial morphology in diabetic rats" Current Eye Research, vol. 6, No. 2, 1987, pp. 391–397, XP002110640 the whole document (Copy submitted to USPTO by WIPO).

Ao S Et Al: "Characterization of a Novel Aldose Reductase Inhibitor, FR74366, and Neuropathy in the Rat" Metabolism, Clinical and Experimental, vol. 40, No. 1, Jan. 1, 1991, pp. 77–87, XP000654446 ISSN: 0026–0495 the whole document (Copy submitted to USPTO by WIPO).

Tsubota K.: "New approaches to dry–eye therapy." International Ophthalmology Clinics, (1994) 34/1 (115–128)., XP002120709 p. 115, paragraph 1 figure 1 page 122, paragraph 3 (Copy submitted to USPTO by WIPO).

Fujishima H Et Al: "Improvement of corneal sensation and tear dynamics in diabetic patients by oral aldose reductase inhibitor, ONO–2235: a preliminary study." Cornea, (1996 Jul.) 15 (4) 368–75., XP002120710 the whole document (Copy submitted to USPTO by WIPO).

Awata T Et Al: "Effect of an aldose reductase inhibitor, CT–112, on healing of the corneal epithelium in galactose–fed rats." Journal of Ocular Pharmacology, (1988 Fall) 4 (3) 195–201., XP002120711 the whole document (Copy submitted to USPTO by WIPO).

Tsubota K Et Al: "The effect of aldose reductase inhibitor on the corneal epithelium." Cornea, (Mar. 1993) 12 (2) 161–2., XP000852574 the whole document (Copy submitted to USPTO by WIPO).

International Search Report and International Preliminary Exam Rpt.

*Primary Examiner*—Zohreh Fay
(74) *Attorney, Agent, or Firm*—Sughrue Mion, PLLC

(57) ABSTRACT

The ophthalmic composition of this invention are used for treatment of diabetic corneal lesion and/or for treatment of deteriorated corneal esthesia, which comprises, as an active ingredient, a compound represented by the general formula (I):

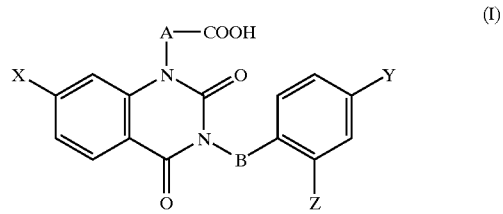

wherein
  A and B are independently lower alkylene,
  X, Y, and Z are independently halogen,
or a pharmacologically acceptable salt thereof.

In addition, the ophthalmic composition of this invention are used for treatment of non-diabetic corneal lesion, for treatment of dry eye syndrome, and/or for treatment of hypolacrimation which comprises, as an active ingredient, an aldose reductase inhibitor.

The ophthalmic compositions of this invention are effective for treatment of at least one disease selected among corneal lesion, deteriorated corneal esthesia, dry eye syndrome, and hypolacrimation.

2 Claims, No Drawings

OPHTHALMIC COMPOSITION

This is a continuation of application No. 09/485,414 (Confirmation No. 1884) filed Feb. 10, 2000, now U.S. Pat. No. 6,403,598, which is a National Stage Application of PCT/JP99/00369 filed Jan. 29, 1999, the disclosure of which is incorporated herein by reference.

TECHNICAL FIELD

This invention relates to ophthalmic compositions, in particular, those for treatment of corneal lesions, those for treatment of deteriorated corneal esthesia, those for treatment of dry eye syndrome, and those for treatment of hypolacrimation.

PRIOR ART

Corneal lesions are caused by defects in the corneal tissue. Defects in the epithelium generally give rise to subjective symptoms including foreign body sensation, eye pain, photophobia, tear secretion, etc. Defects in the corneal tissue are called epithalaxia or erosion when they are restricted only in the epithelium, and corneal ulcer when they extend from the Bowman's membrane to the parenchyma.

There are various possible factors involved in corneal lesions, including pathological factors such as diabetes, inflammation, allergy, microorganisms (virus, bacteria, fungi, etc.) etc., chemical factors such as cytotoxicity by chemicals, caustic effect by acids or alkalis, etc., and physical factors such as dryness (dry eye syndrome, etc.) and trauma due to foreign bodies (contact lens, etc.), burn, etc. It has recently been reported that antiseptics contained in eye drops such as benzalkonium chloride and chlorobutanol, antibiotics of the aminoglycoside series, non-steroidal antiphlogistics, IDU, pimaricin, etc. impair the corneal epithelium.

Various treatments have been attempted depending on the site affected and the severity of the corneal lesion. In addition to physical treatments such as instillation of antibiotic-containing ointment plus pressure eye-patch treatment, use of therapeutic soft contact lens, and corneal superficial puncture, instillation of fibronectin, hyaluronic acid, or a high osmotic agent is currently employed. From the viewpoint of treatment of diabetic complications, it has been reported that aldose reductase inhibitors are effective in treatment of diabetic corneal lesions. However, for example in cases where the symptoms have become aggravated so that the keratoepithelium becomes detached from the corneal parenchyma, satisfactory recovery cannot be attained at present with any of the treatments described above. Thus the treatments desired are those effective even in considerably progressive corneal lesions where the epithelium has been detached or defected.

The cornea is one of the most sensitive tissues on the body surface, and sensory nerve endings are distributed all over the cornea. Therefore when the corneal esthesia remains normal, the patient can notice the pain due to pathological conditions or lesions in cornea. When the corneal esthesia is deteriorated, however, no subjective symptoms are noticed and this promotes to further aggravation of the corneal lesions.

Factors that are known to deteriorate corneal esthesia include aging, diseases (corneal herpes, diabetes, etc.), use of contact lens, and ophthalmologic surgery (surgery for cataract, corneal transplantation, surgery for retinal detachment, etc.). Not only for treatment but also for prevention of progress of the pathological conditions, treatments that may normalize the subjective symptoms of the patients, i.e. agents that may improve the deteriorated corneal esthesia due to various diseases are being desired.

One of the opthalmologic symptoms that became lately the center of wide interest is dry eye syndrome. Dry eye syndrome is defined as "the condition where the tear quantity has been decreased or tear quality has become abnormal, irrespective of whether the keratoconjunctival lesion is present or absent" (Yamada, N., et al., Folia Ophthalmol. Jpn., 43, 1289–1293 (1992)), including dry eye syndrome noted in diseases such as hypolacrimation, alacrima, xerophthalmia, Sjögren's syndrome, dry keratoconjunctivitis, Stevens-Johnson syndrome, ocular pemphigoid, marginal blepharitis, diabetes, etc. dry eye syndrome noted after surgery for cataract, or accompanied with allergic conjunctivitis, etc., and dry eye syndrome observed in hypolacrimation due to increased VDT (visual display terminal) tasks or dry air in an air-conditioned room.

There are various causes of dry eye syndrome some of which remain unidentified. Dry eye syndrome is treated only by administration of artificial tears for increase of the quantity of tear retained within the conjunctival sac to relieve the subjective symptoms, or by prevention of eyes from drying. It has been desired that substances capable of bringing about satisfactory treatment including improvement of hypolacrimation are provided.

Tear secretion is classified into basal tear secretion and reflex tear secretion. Basal tear secretion means tear secretion under ordinary conditions with the eyelid open, being considered to be mainly from the accessory lacrimal glands (Krause gland, Wolfring gland, etc.). On the other hand, reflex tear secretion means tear secretion in the presence of some stimulation to the keratoconjunctival surface, nasal mucosa, etc. or accompanied with mental changes such as grief and joy. It is considered to be from the main lacrimal gland. Therefore improvement of decreased basal tear secretion, i.e. tear secretion under ordinary conditions with the eyelid open, is particularly important as judged from the symptoms of dry eye syndrome.

DISCLOSURE OF THE INVENTION

This invention intends to solve the problems described above, and one of the objectives is to provide ophthalmic compositions effective in treatment of at least one disease selected among corneal lesion, deteriorated corneal esthesia, dry eye syndrome, and hypolacrimation.

The inventors have eventually found as the result of their researches that the compounds represented by the general formula (I):

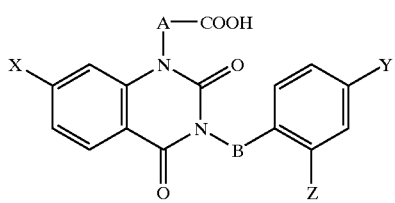

wherein, A and B are independently lower alkylene, and X, Y, and Z are independently halogen, are excellent improvement of diabetic corneal lesion and deteriorated corneal esthesia.

The inventors have also found that the compounds capable of inhibiting aldose reductase including the compounds represented by the above-mentioned general formula (I) are excellent in improvement not only of diabetic corneal lesion but also of non-diabetic corneal lesions, and that the compounds are excellent in improvement of dry eye syndrome, especially hypolacrimation including diminished basal tear secretion. Thus, they completed this invention.

The invention is explained in detail in the following.

(1) An ophthalmic composition for treatment of diabetic corneal lesion and/or for treatment of deteriorated corneal esthesia of which comprises, as an active ingredient, a compound represented by the general formula (I):

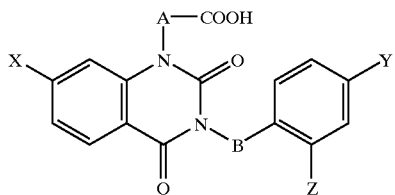

wherein, A and B are independently lower alkylene and X, Y, and Z are independently halogen (named the compound hereinafter), or a pharmacologically acceptable salt thereof.

(2) The ophthalmic composition described in (1) wherein in the general formula (I) A and B are independently methylene, X is chlorine, Y is bromine, and Z is fluorine atom.

(3) The ophthalmic composition described in (1) or (2) that are used for treatment of diabetic corneal lesion.

(4) The ophthalmic composition described in (1) or (2) that are used for treatment of deteriorated corneal esthesia.

(5) The ophthalmic composition described in any of (1) to (4) that are in the form of preparations for eye local administration.

(6) An ophthalmic composition for treatment of non-diabetic corneal lesions which comprises, as an active ingredient, an aldose reductase inhibitor.

(7) An ophthalmic composition for treatment of dry eye syndrome, which comprises, as an active ingredient, an aldose reductase inhibitor.

(8) An ophthalmic composition for treatment of hypolacrimation, which comprises, as an active ingredient, an aldose reductase inhibitor.

(9) The ophthalmic composition described in any of (6) to (8), wherein the aldose reductase inhibitor is a compound represented by the general formula (I):

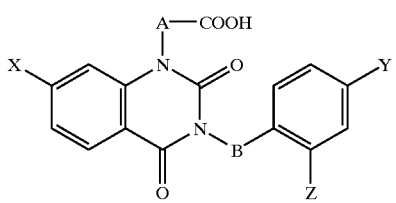

wherein A and B are independently lower alkylene, and X, Y, and Z are independently halogen, or a pharmacologically acceptable salt thereof.

(10) The ophthalmic composition described in (9), wherein A and B are methylene, X is chlorine, Y is bromine, and Z is fluorine.

(11) The ophthalmic composition described in any of (6) to (10) which are in the form of preparations for eye local administration.

(12) A method for treating diabetic corneal lesion and/or deteriorated corneal esthesia which comprises administering an effective amount of a compound represented by the general formula (I):

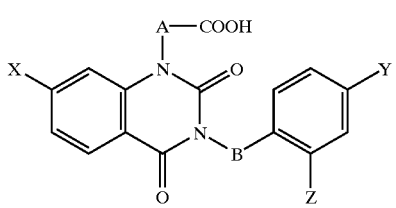

wherein A and B are independently lower alkylene, and X, Y, and Z are independently halogen, or a pharmacologically acceptable salt thereof, to a subject in need of a treatment of diabetic corneal lesion and/or deteriorated corneal esthesia.

(13) A method for treating non-diabetic corneal lesion which comprises administering an effective amount of an aldose reductase inhibitor to a subject in need of a treatment of non-diabetic corneal lesion.

(14) A method for treating dry eye syndrome which comprises administering an effective amount of an aldose reductase inhibitor to a subject in need of a treatment of dry eye syndrome.

(15) A method for treating hypolacrimation which comprises administering an effective amount of an aldose reductase inhibitor to a subject in need of a treatment of hypolacrimation.

(16) Use of a compound represented by the general formula (I):

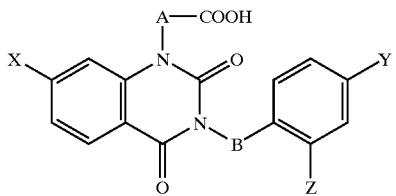

wherein A and B are independently lower alkylene, and X, Y, and Z are independently halogen, or a pharmacologically acceptable salt thereof, in the manufacture of an ophthalmic composition for the treatment of diabetic corneal lesion and/or deteriorated corneal esthesia.

(17) Use of an aldose reductase inhibitor in the manufacture of an ophthalmic composition for the treatment of non-diabetic corneal lesion.
(18) Use of an aldose reductase inhibitor in the manufacture of an ophthalmic composition for the treatment of dry eye syndrome.
(19) Use of an aldose reductase inhibitor in the manufacture of an ophthalmic composition for the treatment of hypolacrimation.

BEST MODE FOR CARRYING OUT THE INVENTION

The terms in the general formula (I) of this specification are defined as follows:

A and B are independently lower alkylene. Lower alkylene as used in this specification mean straight or branched alkylene groups having 1 to 6 carbon atoms, preferably 1 to 4 carbon atoms. In the concrete, they are methylene, ethylene, trimethylene, propylene groups, and the like, among which methylene and ethylene groups are desirable.

X, Y, and Z are independently halogen (chlorine, bromine, fluorine, iodine), and it is particularly desirable when X is chlorine, Y is bromine, and Z is fluorine.

In this invention the compound of the formula (II):

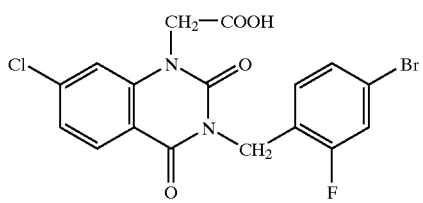

(II)

having methylene for each of A and B, chlorine for X, bromine for Y, and fluorine for Z in the general formula (I), i. e. [3-(4-bromo-2-fluorobenzyl)-7-chloro-2,4-dioxo- 1,2,3, 4-tetrahydroquinazolin-1-yl]acetate, is particularly suitable.

The compound and pharmacologically acceptable salts thereof included in this invention as the active ingredient are publicly known compounds, which can be produced for example with the method described in the Japanese Published Unexamined Patent Publication No. Sho 62- 96476 (European Patent Publication No. 0218999, U.S. Pat. No. 4,734,419) or a method based on this method.

Pharmacologically acceptable salts of the compound in this invention include salts with basic compounds such as inorganic bases (e.g. sodium, potassium, calcium, magnesium, aluminum, ammonium, etc.), and organic bases (e.g. primary amines such as ethanolamine; secondary amines such as diethylamine, diethanolamine, dicyclohexylamine, N,N'-dibenzylethylenediamine, etc.; tertiary amines such as trimethylamine, triethylamine, pyridine, picoline, triethanolamine, etc.; and so on) and the like.

The compound and pharmacologically acceptable salts thereof are effective in prevention, cure, relief/arrestation/ relief of development of symptoms of diabetic corneal lesions, and in improvement of deteriorated corneal esthesia in mammals including man, ox/cow, horse, dog, mouse, and rat etc., being the active ingredient in the ophthalmic composition comprising preparations for treatment of diabetic corneal lesion and/or those for treatment of deteriorated corneal esthesia in mammals.

This invention also provides ophthalmic compositions of which active ingredient is an aldose reductase inhibitor. The fact that compounds that can inhibit aldose reductase are excellent in treatment of non-diabetic corneal lesions as well as symptoms of dry eye syndrome, particularly hypolacrimation including decreased basal tear secretion, is a new finding.

Aldose reductase inhibitors included in this invention as the active ingredient are not specified if they can inhibit aldose reductase, being exemplified in the concrete by the compounds represented by the general formula (I), particularly the compound of the formula (II), and also by epalrestat, ponalrestat, tolrestat, sorbinil, methosorbinil, imirestat, 2,3-dihydro-2,8-bis(1-methylethyl)-3-thioxo-4H- 1,4-benzoxazine-4-acetic acid (AD5467), 6-fluoro-2,3-dihyro-2', 5'-dioxo-(2S-cis)-spiro[4H-1-benzopyran-4,4'-imidazolidine]-2-carboxyamide (SNK-860), 8-chloro-2',3'-dihydrospiro[pyrolizine-3,6'(5, H)-pyrolo [1,2,3-de]-[1,4] benzoxazine]2,5,5'-trion (AND138), and 5-(3-ethoxy-4-pentyloxyphenyl)-2,4-thiazolidinedion (CT-112), etc. Particularly suitable are the compounds represented by the general formula (I), especially the compounds shown by the formula (II).

Aldose reductase inhibitors are effective in prevention, cure, relief/arrestation/relief of development of symptoms of diabetic corneal lesion, and in cure of symptoms of dry eye syndrome, particularly in improvement of hypolacrimation including decreased basal tear secretion in mammals including man, ox/cow, horse, dog, mouse, and rat, etc. They are the active ingredient in the ophthalmic composition for mammals comprising preparations for treatment of non-diabetic corneal lesion, for treatment of dry eye syndrome, and/or for treatment of hypolacrimation.

As described above, diabetic corneal lesion in this invention means various corneal lesions derived from diabetes, including, in the concrete, diabetic punctate superficial keratoepitheliosis, diabetic recurrent erosion of keratoepithelium, and diabetic delayed defect of keratoepithelium. Non-diabetic corneal lesions are, as described above, those caused by non-diabetic pathological, such as inflammation, allergy, microorganisms, chemicals, caustic effect of acids or alkalis, dryness, foreign bodies, burn, etc. Deteriorated corneal esthesia in this invention means the pathological conditions where the corneal esthesia has been deteriorated as the result of aging, diseases such as corneal herpes and diabetes, etc., use of contact lens, and ophthalmologic surgery (surgery for cataract, corneal transplantation, surgery for retinal detachment, etc.). Diseases accompanied with dry eye syndrome include, as described above, hypolacrimation, alacrima, xerophthalmia, Sjögren's syndrome, dry keratoconjunctivitis, Stevens-Johnson syndrome, ocular pemphigoid, marginal blepharitis diabetes, etc. and dry eye syndrome is also noted after surgery for cataract, or accompanied with allergic conjunctivitis, etc. Dry eye syndrome is observed in hypolacrimation due to increased VDT tasks or dry air in air-conditioned rooms. Hypolacrimation means abnormal (decreased or stopped) tear secretion due to some causes, including abnormal basal tear secretion.

Treatment with the ophthalmic composition includes all controls, including prevention, cure, relief/arrestation/relief of development, etc. The treatment of corneal lesion is also effective in intractable corneal lesion in advanced conditions, i.e. with advanced erosion or detachment.

Ophthalmic compositions of this invention may be administered orally or parenterally, but use in the form of preparations for eye local administration is particularly desirable when the avoidance of the influence on other areas of the cardiovascular system and the significance of their actual effectiveness, etc. are taken into account.

Such dosage forms include eye drops, eye ointments, powders, granules, tablets, capsules, injections, etc., among which eye drops and eye ointments are particularly suitable. Preparations in such dosage forms can be produced with the conventional means.

Aqueous solutions and diluents for suspensions used in preparation of eye drops are distilled water, physiological saline, and the like, and non-aqueous solutions and diluents for suspensions include vegetable oil, liquid paraffin, mineral oil, propylene glycol, p-octyldodecanol, etc.

In addition, various additives may be contained in eye drops as needed, including buffering agents, isotonizers, preservatives, thickeners, stabilizers, antizoxidants, pH-adjusting agents, chelating agents, etc. Buffering agents are added to keep the pH constant, for example at 5.0 to 8.0, including borate buffer, citrate buffer, tartrate buffer, phosphate buffer, acetate buffer, etc. Such a buffer is added in an amount that is suitable for the purpose of buffering, i.e. that can keep the pH value constant in the range as described above.

Isotonizers are added to make the preparation isotonic with the tear, including sugars such as glucose, mannitol, sorbitol, etc.; polyhydric alcohols such as glycerol, polyethylene glycol, propylene glycol, etc.; and salts such as sodium chloride, sodium citrate, etc. Such an isotonizer is added in an amount that makes the osmotic pressure of the eye drop equal to that of the tear. Preservatives used are benzalkonium chloride, parabens, chlorobutanol, etc. As pointed out above, some preservatives such as benzalkonium chloride, chlorobutanol, etc. have been reported to impair the cornea, but these preservatives may be added because the preparations of this invention are capable of improving the corneal lesion.

Thickeners that can be used include glycerol, carboxymethyl cellulose, carboxyvinyl polymers, etc.; stabilizers such as sodium sulfite, propylene glycol, etc.; antioxidants such as ascorbic acid, sodium ascorbate, tocopherol, sodium thiosulfate, etc.; pH-adjusting agents such as hydrochloric acid, citric acid, phosphoric acid, acetic acid, tartaric acid, sodium hydroxide, potassium hydroxide, sodium carbonate, sodium bicarbonate, etc.: and chelating agents such as sodium edetate, sodium citrate, etc.

Eye drops are prepared by aseptic manipulation, or sterilization is performed at a suitable stage of preparation.

Eye ointments can be aseptically prepared by mixing the active ingredient into the base usually used for preparation of eye ointments followed by formulation into pharmaceutical preparations with a conventional method. Bases for eye ointments are exemplified by vaseline, jelene 50, plastibase, macrogol, etc., and surfactants may be added to increase hydrophilia. Additives described above, for example preservatives, may be contained in eye ointments as needed.

In addition, ingredients having pharmacological activity different from that of the ingredient of this invention may be added as needed to the pharmaceutical preparations of this invention if they are compatible to the purpose of the invention.

The dose and dosing frequency of the active ingredient of this invention vary according to the symptoms of the disease to be treated, age and body weight of the patient, dosage form, treatment duration, therapeutic effect desired, etc. In general, for local ophthalmic administration, it brings about a satisfactory effect for an adult, that in case of use as an eye drop, of the preparation containing 0.001 to 10.0 w/v %, preferably 0.01 to 1.0 w/v %, of the compound of this invention or a pharmacologically acceptable salt thereof or an aldose reductase inhibitor may be administered several times, preferably 1 to 6 times in an eye, a day and several drops, preferably 1 to 4 drops at a time, and in case of use as an eye ointment, of the preparation containing 0.001 to 10.0 w/v %, preferably 0.01 to 1.0 w/v %, of the compound of this invention or a pharmacologically acceptable salt thereof or an aldose reductase inhibitor may be applied several times, preferably 1 to 6 times in an eye, a day.

In this invention, one active ingredient alone or two or more active ingredients in combination may be contained in the preparation. In the preparation that contains two or more active ingredients, the amount of each ingredient may be determined appropriately according to the therapeutic effect and safety of each ingredient.

EXAMPLES

This invention is explained in the concrete in the Examples described below, and the invention is not limited at all by these Examples.

Experimental Example 1

Influence on the Repair Process of the Wound of Keratoepithelial Detachment in Alloxan-induced Diabetic Rabbits 1) Test Animals and Procedures to Induce Diabetes Alloxan monohydrate (Lot No. DLJ5619, M.W. 160.09: Wako Pure Chemical Industries, LTD.) of 80 mg/kg was dissolved in 2 mL of physiological saline, and the solution was administered once intravenously of male Japanese albino rabbits [Std: JW/CSK] (11-week-old) to induce diabetes.

Blood glucose was determined weekly after administration of alloxan monohydrate: the mean blood glucose was increased from $142.2 \pm 4.7$ mg/dL (mean±S.E.; The same is applicable hereinafter.) before administration to $522.5 \pm 13.7$ mg/dL at 1 week, and this elevated level persisted thereafter. Animals with this alloxan-induced diabetes were used in the experiment.

2) Detachment of Keratoepithelium

Under nembutal anesthesia a circular filter paper of TOYO No. 2 7.0 mm in diameter permeated with 7 $\mu$L of n-heptanol was kept in contact with the surface at the central part of the cornea for 1 minute, and the keratoepithelium was detached by removal of the filter paper from the cornea. Then the surface of the wound due to detachment was washed thoroughly with physiological saline.

3) Measurement of the Area of the Wound of Keratoepithelial Detachment

The cornea was stained with fluorescein, and photographs of the anterior ocular segment were taken with the Medical Nikkor Lens attached with a yellow filter (Kodak WRATTEN No.12) and the front part of the flash attached with a blue filter (Kodak WRATTEN No.47). On the projected photographs magnified to the same degree, the stained area was measured with the planimeter. This area was taken as the area of the wound of keratoepithelial detachment (un-repaired region).

The test substance was instilled every 4 hours after the keratoepithelial detachment (the first instillation was made immediately after preparation of the wound of keratoepithelial detachment).

Twelve hours after the keratoepithelial detachment, the area of the wound was measured. Then its relative value was calculated by taking the area of the wound immediately after the keratoepithelial detachment as 100. This relative value was used to assess the extent of repair.

4) Method of Administration

The compound of the formula (II), i.e. [3-(4-bromo-2-fluorobenzyl)-7-chloro-2,4-dioxo-1,2,3,4-tetrahydroquinazolin-1-yl]acetate, an active ingredient of this invention, was used for preparation of a 0.1% eye drop, and the eye drops were used as the test substance. The vehicle control was the vehicle of the eye drop after exclusion only of the active ingredient.

Every 4 hours from immediately after the keratoepithelial detachment, the test substance was instilled at the volume of 30 μL/eye into the unilateral eye of a rabbit by using a Pipetman, while the vehicle control was instilled at 30 μL/eye into the contralateral eye.

5) Statistical Analysis

The area of the un-repaired wound in the test substance-instilled eye was compared with that in the vehicle control substance-instilled eye with the Student's t-test. The results are shown in Table 1.

TABLE 1

|  | Relative area of wound of keratoepithelial detachment 12 hours after keratoepithelial detachment (%) | n |
|---|---|---|
| Test group | 89.0 ± 2.7* | 5 |
| Control group | 96.5 ± 2.0 | 10 |

*$p < 0.05$

The difference was judged to be significant because the level of significance was below 5%.

Experimental Example 2

Influence on the Repair Process of the Wound of Keratoepithelial Detachment in Normal Rabbits In the Experimental Example 1, the influence in rabbits with alloxan-induced diabetes was investigated, while the influence in normal (not diabetic) rabbits was investigated in this Example.

1) Test Animals

Ten-week-old male New Zealand White rabbits (weighing 2.07±0.11 kg: mean weight at the start of the experiment) were acclimation period for 7 days, while the animals were examined for the general signs including diarrhea and body weight, etc., and the anterior ocular segment was also observed. Only animals without any abnormality were used in the experiment.

2) Detachment of Keratoepithelium

Keratoepithelial detachment wounds were prepared as described in the Experimental Example 1.

3) Measurement of Area of the Keratoepithelial Detachment Wound

The test substance was instilled every 4 hours after the keratoepithelial detachment (the first instillation was made immediately after preparation of the wound of keratoepithelial detachment).

Twelve hours after the keratoepithelial detachment, the area of the wound was measured, and its relative value was calculated by taking the area of the wound immediately after the keratoepithelial detachment as 100, and the relative value was used to assess the extent of repair. The area of the wound of keratoepithelial detachment was measured as described in the Experimental Example 1.

4) Method of Administration

[3-(4-Bromo-2-fluorobenzyl)-7-chloro-2,4-dioxo-1,2,3,4-tetrahydroquinazolin-1-yl]acetate, an active ingredient of this invention, having aldose reductase-inhibiting effect was used for preparation of 0.2% eye drops, and the eye drops were used as the test substance. The vehicle control was the vehicle of the eye drops simply without the active ingredient.

Every 4 hours from immediately after the keratoepithelial detachment, the test substance was instilled at the volume of 30 μL/eye into the unilateral eye of a rabbit by using a Pipetman, while the control substance was instilled at 30 μL/eye into the contralateral eye.

5) Statistical Analysis

The area of un-repaired wound in the test substance-treated eye was compared with that in the vehicle control treated eye with the Student's t-test. The results are shown in Table 2.

TABLE 2

|  | Relative area of wound of keratoepithelial detachment 12 hours after keratoepithelial detachment (%) | n |
|---|---|---|
| test group | 80.8 ± 2.0** | 6 |
| control group | 88.8 ± 1.0 | 6 |

**$p < 0.01$

The difference was judged to be significant because the level of significance was below 1%.

Experimental Example 3

Influence on the Deteriorated Corneal Esthesia and Hypolacrimation in Alloxan-induced Diabetic Rabbit 1) Test Animals and Procedure to Induced Diabetes Alloxan monohydrate (Lot No. DLJ5619, M.W. 160.09 Wako Pure Chemical Industries, LTD.) of 80 mg/kg was dissolved in 2 mL of physiological saline, and the solution was administered once intravenously of male Japanese albino rabbits [Std: JW/CSK] (11-week-old) to induce diabetes.

Blood glucose was determined once a week on 4 times after administration of alloxan monohydrate: animals having always blood glucose of 300 mg/dL or more were used as diabetic animals in this Experiment.

2) Method of Administration

[3-(4-Bromo-2-fluorobenzyl)-7-chloro-2,4-dioxo- 1,2,3, 4-tetrahydroquinazolin- 1-yl]acetate, an active ingredient of this invention, having aldose reductase-inhibiting effect was used for preparation of a 0.3% eye drops, and the eye drops were used as the test substance. The vehicle control was the vehicle of the eye drops simply without the active ingredient.

At the time of intravenous administration of alloxan, the drug was instilled into both eyes at 30 μL/eye four times a day over 4 consecutive weeks. Sixteen eyes of 8 animals in each of the test substance group and the vehicle control group were subjected to the examination of corneal esthesia and the examination of tear secretion as follows.

3) Examination of Corneal Esthesia

One hour after the second instillation on the day of examination, each animal was fixed in a stainless steel fixator (SHIBATA GLASS WORKS). The central part, the most sensitive part, of the cornea was stimulated 10 times in rapid sequence with a pressure by applying at the right angle a 30 mm nylon thread (Toray Nylon Monofilament, Type 100, No.0.6, diameter $\phi$: 0.027mm, cross section s: 0.0129) of the Cochet-Bonnet type esthesiometer (Handaya Co., Ltd.) so that the nylon thread might be bent only slightly (pressure: 5.19 g/mm$^3$, measured by Handaya), and the number of blink reflex was taken as the corneal esthesia value. The examination was performed before, 2 weeks after and 4 weeks after administration of alloxan.

4) Examination of Tear Secretion (Schirmer's Test)

One hour after the second instillation on the day of examination, each animal was fixed in a stainless steel fixator, and the edge of the Schirmer's test paper (SHOWA YAKUHIN KAKO, Co., Ltd., Lot No.70080) was inserted into the conjunctival sac to cover the ⅓ of the lower eyelid on the ear side. One minute after, the paper was removed, and the length of the moistened part was read from the scale on the paper. The examination was performed before and 4 weeks after administration of alloxan in each group.

5) Statistical Analysis

In both examinations, the test substance group and the vehicle control group were compared with the Williams's test.

The results of the examination of corneal esthesia are shown in Table 3, and those of the examination of tear secretion in Table 4.

TABLE 3

| | Coreneal esthesia value (number of times) | | | |
| --- | --- | --- | --- | --- |
| | Before alloxan | After 2 weeks | After 4 weeks | n |
| test group | 5.6 ± 0.3 | 5.3 ± 0.7** | 5.1 ± 0.6** | 16 |
| control group | 5.3 ± 0.5 | 3.5 ± 0.5 | 2.6 ± 0.4 | 16 |

**$p < 0.01$

TABLE 4

| | tear secretion (mm: Schirmer's test) | | |
| --- | --- | --- | --- |
| | before alloxan | After 4 weeks | n |
| test group | 8.3 ± 0.6 | 7.1 ± 0.4** | 16 |
| control group | 8.2 ± 0.4 | 4.8 ± 0.4 | 16 |

**$p < 0.01$

In both Tables, difference was judged to be significant because the level of significance was below 1%.

Experimental Example 4

Influence on Decreased Basal Tear Secretion and Keratoepithelial Lesion in Rabbits with Dry Eye Syndrome Induced by Trigeminal Denervation.

1) Test Animals

Twenty male Japanese albino rabbits [Std:JW/CSK] were used.

2) Trigeminal Denervation a) Operational Procedure

Urethane (ALDRICH, Lot No.069110Q) was intraperitoneally administered at the dose of 1 g/kg to rabbits of which hair at the head after anesthesia had been shaved.

After disinfection of the shaved area, midline incision of the skin was made from the frontal bone to the ear root, and the periosteum and the muscular tissue around the temporal bone and mandibular articular process were detached. After the detachment, a hole of 2×1.5 cm in size was made in the bone from the parietal medial region to the temporal region by using a bone drill (URAWA KOGYO Co., Ltd., MINITOR.C-130) under the surgical microscope (KONAN CAMERA R& I Inc., PMO-50). Then the dura was detached from the cranial bone while cotton was kept inserted between the temporal bone and the dura. After the detachment was made up to the cranial base, detachment was further made toward the medial border of the petrous part of temporal bone in the cranial cavity, to find the trigeminal nerve in the petrous part. Then the dura of about 1 to 2 mm on the nasal side of the semilunar ganglion was incised. After the incision, the two branches of nerve fascicle, i.e. the first branch of the trigeminal nerve (ocular nerve) and the second branch (maxillary nerve), were pulled laterally and cut with corneoscleral scissors. After confirmation of miosis of the ipsilateral eye immediately after the cut, the cotton kept inserted was removed, and the skin at the head was closed with suture. After the operation, an antibiotic (MYCILLIN SOL®: Meiji) was administered intramuscularly at the dose of 0.1 mL/kg.

The trigeminal denervation was made only on the left eye side, while the trigeminal denervation on the right eye side or sham operation was not made b) Acclimation Period Two-week acclimation period was allowed to pass after the trigeminal denervation.

Only animals that showed decreased basal tear secretion and keratoepithelial lesion in this period were used in the experiment 3) Method of Administration

[3-(4-Bromo-2-fluorobenzyl)-7-chloro-2,4-dioxo- 1,2,3, 4-tetrahydroquinazolin- 1-yl]acetate, an active ingredient of this invention, having aldose reductase-inhibiting effect was used for preparation of 0.03% eye drop, 0.1% eye drop, and 0.3% eye drop, which were used as the test substances. The vehicle control was the base of the eye drops simply without the active ingredient.

From about 2 weeks after the trigeminal denervation, one of the above-mentioned drugs was instilled at the volume of 30 μL/eye four times a day for 2 consecutive weeks. Five eyes of each of the test substance groups and the control group were examined for the basal tear secretion and the keratoepithelial lesion as follows.

4) Examination a) Basal Tear Secretion

Before the start of instillation (Week 0), and 1 week and 2 weeks after instillation, the basal tear secretion was measured one hour after the second instillation on the day of examination.

Keratoconjunctiva was anesthetized by instillation of 4% lidocaine (Xylocaine® 4% for ophthalmology: Fujisawa Pharmaceutical Co., Ltd.), and the eye drop and the tear around the eyelid were wiped off about 5 minutes later.

When loss of keratoconjunctival esthesia was confirmed with the Cochet-Bonnet type esthesiometer, the edge of the Shirmer's test paper was kept inserted into the conjunctival sac for 5 minutes, and the length of the moistened part was read from the scale on the paper.

The basal tear secretion was expressed by the mean per minute calculated from the 4-minute-value obtained by subtraction of the first-1-minute-value from the 5-minute-value of the Shirmer's test, so that the volume of the tear considered to be retained in the conjunctival sac might be excluded.

b) Keratoepitherial Lesion

Before the start of instillation (Week 0), and 1 week and 2 weeks after instillation, the lesion was evaluated one hour after the first instillation on the day of examination.

Each animal was placed in a stainless steel fixator, and given instillation of 50 μL of the mixture of 1% rose bengal and 1% fluorescein, followed by vital staining of the keratoconjunctival epithelium for evaluation of the extent of lesion according to the scoring system shown in Table 5.

TABLE 5

| Score | Stained area of keratoconjunctiva |
| --- | --- |
| 0 | None |
| 0.5 | A part stained slightly |
| 1 | Less than 1/4 |
| 2 | More than 1/4 and less than 1/2 |
| 3 | More than 1/2 and less than 3/4 |
| 4 | More than 3/4 |

5) Results

The results of the examination of basal tear secretion and the of the examination of keratoepithelial lesion are Shown Table 6 and in Table 7, respectively. The reslts of statistical analyses are also shown in the Tables.

TABLE 6

| | Number of eyes | Time point (week) | Basal tear secretion (mm/minute) |
| --- | --- | --- | --- |
| Before operation | 20 | — | 1.28 ± 0.16 |
| Acclimation period | 20 | 1 | 0.39 ± 0.05 [**] |
| | 20 | 2 | 0.38 ± 0.06 [**] |
| Control group | 5 | Before instillation | 0.40 ± 0.15 * |
| | 5 | 1 | 0.58 ± 0.21 [*] |
| | 5 | 2 | 0.54 ± 0.12 [**] |
| Test group 0.03% | 5 | Before instillation | 0.38 ± 0.09 [**] |
| | 5 | 1 | 0.92 ± 0.17 # |
| | 5 | 2 | 1.02 ± 0.09 ##+ |
| Test group 0.1% | 5 | Before instillation | 0.38 ± 0.13 [**] |
| | 5 | 1 | 1.24 ± 0.14 ##+ |
| | 5 | 2 | 1.12 ± 0.11 ##++ |
| Test group 0.3% | 5 | Before instillation | 0.34 ± 0.10 [**] |
| | 5 | 1 | 1.24 ± 0.16 ##+ |
| | 5 | 2 | 1.20 ± 0.15 ##++ | p < 0.05 ##p < 0.01: comparison with the value before instillation in each group (Student's t-test)
*p < 0.05 **p < 0.01: comparison with the value before operation (Student's t-test)
[*]p < 0.05 [**]p < 0.01: comparison with the value before operation (Aspin-Welch test)
+p < 0.05 ++p < 0.01: comparison with the value at the corresponding time point in the control group (Dunnett's test)

TABLE 7

| | Number of eyes | Time point (week) | Keratoepithelial lesion (score) |
| --- | --- | --- | --- |
| Before operation | 20 | — | 0.0 ± 0.0 |
| Acclimation period | 20 | 1 | 2.4 ± 0.2 [**] |
| | 20 | 2 | 2.9 ± 0.2 [**] |
| Control group | 5 | Before instillation | 2.8 ± 0.6 [**] |
| | 5 | 1 | 1.4 ± 0.4 [*] |
| | 5 | 2 | 1.1 ± 0.2 #[*] |
| Test group 0.03% | 5 | Before instillation | 2.8 ± 0.4 [**] |
| | 5 | 1 | 0.5 ± 0.4 [##] |
| | 5 | 2 | 0.2 ± 0.1 [##]++ |
| Test group 0.1% | 5 | Before instillation | 3.0 ± 0.6 [**] |
| | 5 | 1 | 0.4 ± 0.2 ##]+ |
| | | 2 | 0.4 ± 0.2 [##]+ |
| Test group 0.3% | 5 | Before instillation | 3.0 ± 0.5 [**] |
| | 5 | 1 | 0.5 ± 0.4 ## |
| | 5 | 2 | 0.1 ± 0.1 190 #++ | p < 0.05 ##p < 0.01: comparison with the value before instillation in each group (Student's t-test)
[#]p < 0.05 [##]p < 0.01: comparison with the value before instillation (Aspin-Welch test)
[*]p < 0.05 [**]p < 0.01: comparison with the value before operation (Aspin-Welch test)
+p < 0.05 ++p < 0.01: comparison with the value at the corresponding time point in the control group (Dunnett's test)

INDUSTRIAL APPLICABILITY

The ophthalmic compositions of this invention comprising the compound of this invention or a pharmacologically acceptable salt thereof as the active ingredient are effective in prevention, cure, relief of the symptoms, etc. of diabetic corneal lesions, particularly severe diabetic corneal lesion (e.g. in repair of the wound of keratoepithelial detachment), and also in improvement of the deteriorated corneal esthesia. Therefore the ophthalmic compositions of this invention are suggested to be useful for treatment of diabetic corneal lesion and for treatment of deteriorated corneal esthesia.

The ophthalmic compositions of this invention containing the compound or a pharmacologically acceptable salt thereof or an aldose reductase inhibitor as the active ingredient are effective also in prevention, cure, relief of the symptoms, etc. of non-diabetic corneal lesions (e.g. in repair of the wound of keratoepithelial detachment) and in cure of symptoms of dry eye syndrome (e.g. in improvement of hypolacrimation including decreased basal tear secretion). Therefore they are suggested to be useful for treatment of non-diabetic corneal lesion, treatment of dry eye syndrome, and for treatment of hypolacrimation.

What is claimed is:

1. A method for treating diabetic corneal lesion and/or deteriorated corneal esthesia which comprises administering an effective amount of a compound represented by the general formula (I):

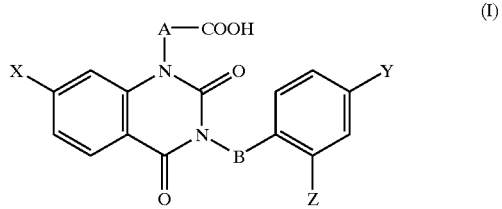

wherein A and B are independently lower alkylene, and X, Y, and Z are independently halogen, or a pharmacologically acceptable salt thereof, to a subject in need of a treatment of diabetic corneal lesion and/or deteriorated corneal esthesia.

2. A method for treating non-diabetic corneal lesion which comprises administering an effective amount of an aldose reductase inhibitor to a subject in need of a treatment of non-diabetic corneal lesion.

* * * * *